United States Patent
Gagliardi et al.

(10) Patent No.: US 6,245,693 B1
(45) Date of Patent: Jun. 12, 2001

(54) LAMINATED COMPOSITE ABSORBENT STRUCTURE COMPRISING ODOR CONTROL MEANS

(75) Inventors: Ivano Gagliardi, Pescara; Mario Guarracino, Silvi Marina; Carlo Toro, Pescara, all of (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/319,750

(22) PCT Filed: Dec. 19, 1997

(86) PCT No.: PCT/US97/23632

§ 371 Date: Jun. 10, 1999

§ 102(e) Date: Jun. 10, 1999

(87) PCT Pub. No.: WO98/27919

PCT Pub. Date: Jul. 2, 1998

(30) Foreign Application Priority Data

Dec. 20, 1996 (EP) .................................... 96120570

(51) Int. Cl.⁷ ................ A61F 13/15; B32B 5/18

(52) U.S. Cl. ................ 442/76; 442/59; 442/96; 604/359; 502/402

(58) Field of Search .............. 428/137; 604/359–364, 604/368; 502/402; 442/59, 76, 96

(56) References Cited

FOREIGN PATENT DOCUMENTS

WO 97/46192 * 12/1997 (WO) ................. A16F/13/15

* cited by examiner

*Primary Examiner*—Elizabeth M. Cole
*Assistant Examiner*—Arti R. Sinah
(74) *Attorney, Agent, or Firm*—Theodore P. Cummings; Matthew P. Fitzpatrick; Kevin C. Johnson

(57) ABSTRACT

The laminated absorbent structure has absorbent gelling material (26) and a first odour absorber (24) each held between separate containing layers (2,4,6). The absorbent gelling material also separates a fluid-receiving surface from the first odour absorber. A second absorber may be a coating sprayed onto the layer (2) so that it is between the gelling material and the first surface. The first absorber is active when not wetted and the second odour absorber is active when wetted. The containing layers are fibrous layers and absorbent gelling material and the odour absorbers are in particle or powder form.

9 Claims, 1 Drawing Sheet

LAMINATED COMPOSITE ABSORBENT STRUCTURE COMPRISING ODOR CONTROL MEANS

FIELD OF THE INVENTION

The present invention relates to laminated absorbent structures comprising an odour control means, suitable for use in absorbent articles, in particular sanitary napkins and pantiliners.

BACKGROUND OF THE INVENTION

Disposable absorbent articles are well known and all have absorbent elements for absorbing and retaining body fluids; an absorbent element must be able to acquire liquid rapidly and to distribute it internally so as to prevent leakage and must also have a good capacity to retain the fluids when subjected to the normal pressures of use.

Whilst the primary focus of absorbent articles remains the ability of these articles to absorb and retain fluids, another important area of development in this field is the control of odourous compounds contained within the absorbed fluids or their degradation products. There are a wide range of compounds which may be present in an absorbent article during use which result in the formation of malodourous. These compounds include fatty acids, ammonia, amines, sulphur containing compounds and ketones and aldehydes.

The art is replete with descriptions of various odour control agents for use in absorbent articles in order to address the problem of malodour formation. For example, acidic, basic and neutral odour control agents are known.

Odour control means comprising mixtures of different types of odour control agents are widely used in absorbent articles in order to increase the effectiveness of the odour control means against the various malodorous compounds associated with the use of absorbent articles following the absorption of aqueous body fluids.

For example EPO 348978 discloses an absorbent article comprising an odour control system wherein the neutral odour control particles are selected from carbon, clays, silica, zeolites and molecular sieves. WO 91/12029 discloses the combination of zeolites and absorbent gelling materials to provide improvement in the control of ammonia odours.

Although mixtures of different odour control agents can perform well their action in controlling the odours associated with the use of absorbent articles, interactions between certain odour control agents and the absorbed aqueous body fluids, or between different odour control agents can at least partially impair the effectiveness of known odour control means.

U.S. Pat. No. 5,230,958 describes a process for incorporating an odour control means in powder form into a hydrophilic, swellable, water-insoluble polymer, in order to get a flexible structure containing the odour control particles in a dust-free stable form. Possible interactions between two incompatible odour control agents can be avoided by incorporating these odour control agents separately in two different substrates of the structure.

The odour control compounds described in the patent typically perform their action when liquid is absorbed by the hydrophilic polymer that incorporates them, and therefore liquid cannot be prevented from reaching those odour control compounds that can be negatively influenced by absorbed liquid.

U.S. Pat. No. 5,037,412 describes a sanitary article in which odour control agents of acidic, basic and neutral type that are active preferably in their anhydrous state are incorporated in such a way that they are not reached by absorbed fluid, and therefore remain substantially dry, for at least a substantial period of time after absorption of fluid by the sanitary article. The odour control agents are mixed together and positioned in the sanitary article at locations that are not likely to be reached by the absorbed fluid for a substantial period of time after absorption, e.g. between the absorbent core and the backsheet, along the periphery of the backsheet itself, or in the centre of the absorbent core, or even along its periphery.

While these structures are capable of avoiding interactions between absorbed fluids and odour control agents that can be negatively influenced by them, they have a rather complex structure, while at the same time the odour control means is a simple mixture of different odour control agents, all of them intended to act in their dry state.

In European Application EP-A-510619 an absorbent article is described which comprises an odour control complex including a combination of at least 2 agents selected form a group which includes zeolites and silica gels. The effectiveness of at least some of the odour control agents can be enhanced by disposing the liquid absorbent material, typically a fluff of cellulose fibres, between the topsheet and the odour control agents themselves, in order to reduce the exposure of the agents to body fluids. The structures described are fairly complex and rely on a combination of several different components and odour control agents each performing one different task among fluid absorption, pH buffering, and odour controlling. Moreover, when odour control agents are incorporated in these structures in particulate form, it is difficult to avoid loss or spillage of these particles from the structure, both during the production, and during the use within the sanitary product that incorporate it. These structures are therefore not suitable for production as a semi-finished product intended to be sold and stored separately in form of a continuous web-like structure, e.g. wound in a roll, which can subsequently be fed to a production line of sanitary articles.

Hence, there still exists a need to provide an absorbent structure that comprises an odour control means and is simple to produce while having a better effectiveness. It has now been observed that this need can be addressed by an absorbent structure in which a combined synergic effect is achieved between absorbent gelling material and different odour control agents, by which the performances of the odour control agents that act preferably in dry conditions, and optionally of those that are active in solution, are enhanced. The structures also take advantage of the combined activity of its components in performing two or more actions among fluid absorption, pH buffering, and odour control. Moreover, they can be produced as a semi-finished product, while being substantially free from loss or spillage of incorporated particulate material.

SUMMARY OF THE INVENTION

The present invention relates to a laminated absorbent structure for absorbing aqueous body fluids and for providing odour control, having a first surface intended to receive the body fluids and a second surface aligned approximately opposite to the first surface, the laminated absorbent structure comprising first odour control means for absorbing malodours and further comprising an absorbent gelling material. The first odour control means and the absorbent gelling material are each contained between separating containing layers, the first odour control means being separated from the first surface by the absorbent gelling material.

BRIEF DESCRIPTION OF THE DRAWINGS

While the specification concludes with claims particularly pointing out and distinctly claiming the present invention, it is believed that the present invention will be better understood from the following description in conjunction with the following drawings:

DETAILED DESCRIPTION OF THE INVENTION

Figure 1:
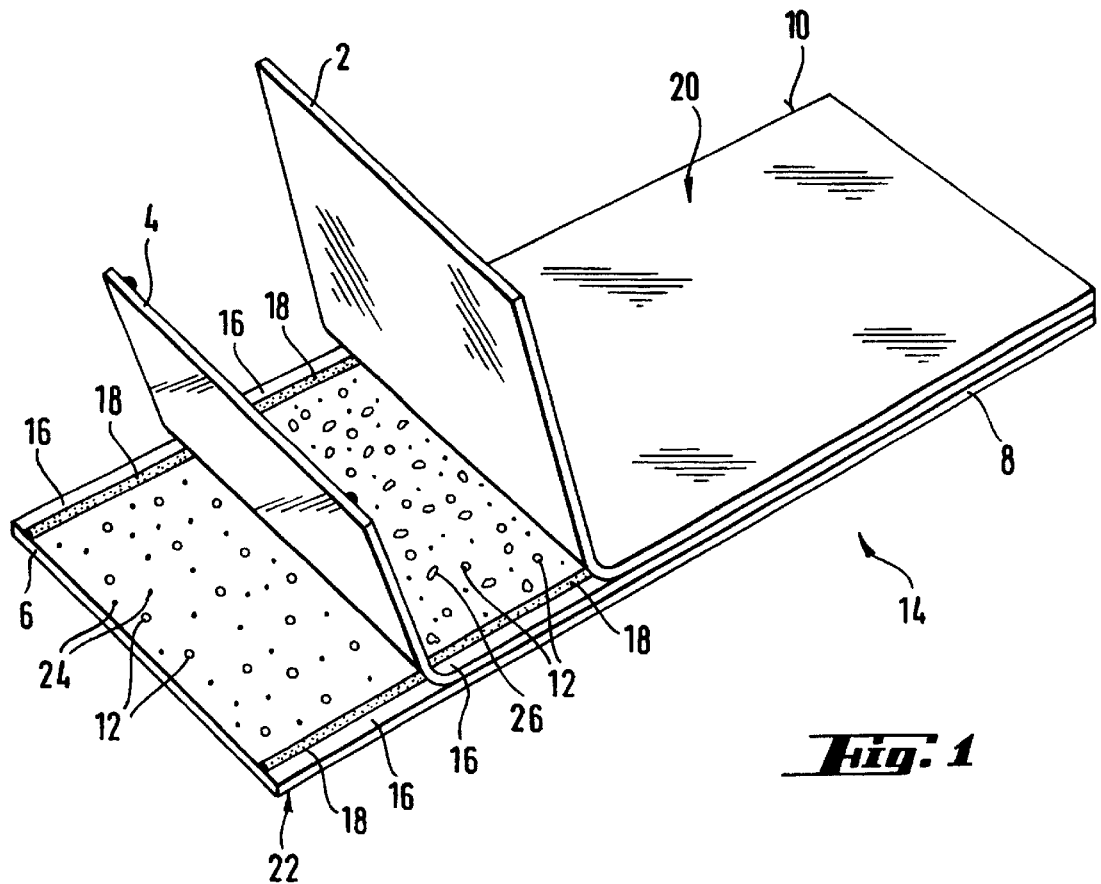
FIG. 1 is a perspective view of a laminated structure according to the present invention, with two of the three containing layers partially raised.

The present invention relates to laminated absorbent structures for absorbing aqueous body fluids and for providing control of odorous compounds contained within the absorbed fluids or their degradation products. The laminated absorbent structures will be described herein in relation to their use in disposable absorbent articles, e.g. sanitary napkins or catamenials, typically as absorbent elements. The laminated absorbent structures of the present invention can constitute integrally the absorbent element of a disposable absorbent article, or they can be comprised therein as part of the absorbent element, or in any case they can constitute an element of a disposable absorbent article.

Disposable absorbent articles, such as for example sanitary napkins, pantiliners, incontinent pads, or diapers, typically comprise a fluid pervious topsheet, a fluid impervious backsheet, that can optionally be water vapour and/or gas pervious, and an absorbent element comprised therebetween.

The term "sanitary napkin", as used herein, refers to an article which is worn by females adjacent to the pudendal region and which is intended to absorb and contain the various body fluids which are discharged from the body (e.g., vaginal discharges, menses, and/or urine) and which is intended to be discarded after a single use.

The term "use", as used herein, refers to the period of time that starts when the absorbent article is actually put in contact with the anatomy of the user.

According to the invention the laminated absorbent structure comprises a first odour control means and an absorbent gelling material, each contained between separating containing layers, by "separating containing layers" being meant layers that contain between them the absorbent gelling material and the first odour control means, at the same time separating them from each other and being distinct from both the absorbent gelling material and the first odour control means.

The development of unpleasant odours from body fluids as sweat, menstrual blood, vaginal discharges, or urine, are basically due to two different causes: a) malodorous chemical compounds already contained in the body fluids; and b) malodorous chemical compounds produced by the bacterial metabolism when the bacteria come in contact with body fluids for a prolonged period of time.

Means for controlling the odours associated with body fluids and their incorporation in disposable absorbent articles are widely known in the art, and various odour-control agents have been disclosed in the literature.

Different classes of odour-control agents are known in the art according to their different mechanisms of action. Disposable absorbent articles can comprise only one odour-control agent, or combinations of various odour-control agents, optionally belonging to different classes and therefore performing different actions for the control of unpleasant odours associated with body fluids.

A first class of odour-control agents is constituted by those compounds that interfere with the bacterial metabolism, in order to avoid or to reduce the production of malodorous metabolites from the body fluids; such agents can be bactericides or bacteriostats and are typically available as water-soluble compounds.

A second class of odour-control agents comprises those compounds, typically in particulate form, that are capable of adsorbing within their structure the odoriferous substances, both those already present in the body fluids as such and those produced by the bacterial metabolism.

Another class of odour-control agents comprises perfumes that essentially mask the unpleasant odours; moisture-activated encapsulated perfume particles can also be used, in which the perfumes are released only when the material is wetted, to provide their action during the use of the product, and to optionally avoid interaction with other odour-absorbing agents before the product is used, if such a combination is actually used as the odour-control means.

A broader distinction can be made among the odour control agents known in the art. Some odour control agents are active preferably in dry conditions, that is, when substantially not wetted by absorbed fluids. Moreover, negative influence of liquid is even more enhanced when the pH conditions are far from neutrality, which is most likely to occur in structures for absorbing body fluids, owing to the degradation of the fluids themselves. Other odour control agents perform their action in solution, and therefore must be wetted by the absorbed fluid.

Odour control agents belonging to the above mentioned first class are typically active in solution; this is true for some perfume substances too, for example the moisture-activated encapsulated perfumes.

On the contrary, odour control agents of the second class are typically active towards gaseous odorous compounds related to the absorbed fluid by means of. e.g. an adsorption mechanism, and therefore better perform their action in substantially dry conditions.

Bearing in mind this distinction, any odour-control agent known in the art that can be suitably incorporated in absorbent structures for absorbing body fluids, or any suitable combination thereof, can be used in the laminated absorbent structures of the present invention, to provide the article which incorporates this structure as the absorbent element, or at least as part of it, with the benefit of controlling the odours associated with absorbed body fluids.

Among odour-control agents that can be employed in the practice of the present invention can be for example water-soluble antibacterial compounds, which are therefore intended to be active typically in solution. Such compounds include, for example, halogenated phenylene compounds (U.S. Pat. No. 3,093,546), periodic acids (U.S. Pat. No. 3,804,094), various copper compounds, especially copper acetate (U.S. Pat. No. 4,385,632), various quaternary ammonium salts, which are well known for their antibacterial properties, e.g. cetyl pyridinium chloride, and the like.

In a known mode, the odour-control agent can be a water-insoluble particulate odour-absorbing material such as chlorophyll particles, activated carbon granules, charcoal, ion exchange resin (Japanese 87019865), activated alumina, and absorbent zeolite materials, including the well known "molecular sieve" zeolites of the type A and X and the zeolite materials marketed under the trade name ABSCENTS by the Union Carbide Corporation and UOP, and which are typically available as a white powder in the 3–5 micron particle size range. Most of these agents are more effective in dry conditions.

The odour-control agents used in the present invention can also comprise other compounds such as cyclodextrin, chelating agents, parabens, chitin, pH buffered materials, silica gel, clays, diatomaceous earth, polystyrene derivatives, starches, and the like.

Further odour control agents can comprise acidic compounds such as ascorbic acid, stearic acid, boric acid, maleic acid polymers, malonic acid, maleic acid, polyacrylic acid and monopotassium phosphate, or basic compounds such as inorganic salts of carbonates, bicarbonate, phosphate, biphosphate, sulfate, bisulfate, and mixtures thereof, as those described in U.S. Pat. No. 5,037,412, or as the combination of boric acid and sodium tetraborate described in International application WO 94/25077.

A distinction between those agents which are more active in dry conditions as compared to agents typically active in solution can be made by the skilled man.

It is to be understood that the odour-control means employed in the practice of the present invention is not, simply, the odour-control agent, per se, added to the absorbent structure. Rather, the odour-control means comprises any combination of odour-control agents and, optionally, of other materials such as binders. Agglomerates of different odour control agents, e.g. with a binder, can therefore also be used, such as for example an agglomerate of zeolite and silica in particle form, as that described in European application EP 96109175.8, filed on Jun. 7, 1996. The odour-control agent, on the other hand, is the specific odour-control compound.

The laminated absorbent structure of the present invention also comprises an absorbent gelling material. As is well-known from recent commercial practice, absorbent gelling materials (sometimes referred to as "super-sorbers") are becoming broadly used in absorbent articles. AGM's are materials which have fluid-absorbing properties. Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those which, upon contact with fluids (i.e., liquids) such as water or body fluids, imbibe such fluids and thereby form hydrogels. These preferred absorbent gelling materials will generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer materials; and (4) polyvalent metal compounds which can form ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization". Typically, commercial absorbent gelling materials have a degree of neutralization somewhat less than 90%.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent and is specified as grams of synthetic urine per gram of gelling agent.

Gel volume in synthetic urine (see Brandt, et al, below) can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, Reissue 32,649. The absorbent gelling materials which are especially useful in the absorbent articles herein are those which have an equilibrium extractables content in synthetic urine of no more than about 17%, preferably no more than about 10% by weight of the absorbent gelling material.

As far as the arrangement of the containing layers is concerned, the laminated absorbent structures of the present invention can be manufactured in various ways well known in the art.

Preferably, the laminated absorbent structures according to the present invention are manufactured from a continuous laminated absorbent structure of a type similar to the thin, layered absorbent structures described in the two International applications WO 94/01069 and WO 95/17868.

FIG. 1 shows a preferred configuration of a laminated absorbent structure 14 formed according to the present invention, with two of the three separating containing layers that form the structure partially raised to show its construction more clearly.

In the laminated absorbent structure of FIG. 1 it is possible to distinguish a first surface 20 which is intended to receive, in use, the body fluids, and a second surface 22 aligned approximately opposite to the first surface 20; in the embodiment illustrated in FIG. 1 the two surfaces 20 and 22 are substantially parallel to each other. When the laminated absorbent structure is incorporated as an absorbent element in a disposable absorbent article, e.g. a sanitary napkin, the first surface 20 is intended to stay, in use, nearer to the user's body, while the second surface 22 is closer to the user's undergarment.

The laminated absorbent structure 14 of FIG. 1 comprises first, second and third containing layers 2, 4, and 6 which are preferably fibrous layers, the containing layer 2 being nearer to the first surface 20 of the laminated absorbent structure 14, while the containing layer 6 is nearer to the second surface 22 and the containing layer 4 is intermediate. The containing fibrous layers 2, 4, and 6 have the same width that is constant along the length of the structure 14, and are superposed so that their respective longitudinal edges 8 and 10 coincide; the containing fibrous layers may be made of various materials such as, for example, paper, wadding, or non-woven fabric; they are preferably made of dry-formed layers, generally referred to as "air laid" layers, of short cellulose fibres having a basic weight of between 20 g/m2 and 150 g/m2.

Alternatively, however, the containing fibrous layer that is nearer to the second surface 22, and that in the embodiment of FIG. 1 corresponds to the containing fibrous layer 6, can consist of a dry-formed mixture of cellulose fibres and bicomponent polyethylene/polypropylene fibres, such as, for example, those sold by Danaklon a/s of Varde, Denmark, as AL-Thermal B and AL-Thermal C.

The laminated absorbent structure 14 further comprises a first odour control means 24 and an absorbent gelling material 26, both in particulate form; each of the odour control means 24 and of the absorbent gelling material 26 is contained between separating containing layers and is preferably in particle or powder form. In the embodiment of FIG. 1 the first odour control means 24 is contained between separating containing layers 4 and 6, while the absorbent gelling material 26 is contained between separating containing layers 2 and 4, with the containing layer 4 therefore comprised between the absorbent gelling material 26 and the first odour control means 24.

In a preferred embodiment of the present invention a thermoplastic, polymeric, organic material 12 in finely divided form, preferably in particle form, is comprised between the fibrous layers 2, 4 and 6 and are mixed both with the first odour control means 24 and with the absorbent gelling material 26, therefore forming two intermediate layers comprised between separating containing fibrous layers 2, 4 and 6. The width of each intermediate layer is less than that of the separating containing layers 2, 4 and 6 that extend beyond the intermediate layers forming longitudinal edge portions 16 at their respective longitudinal edges 8 and 10.

Each pair of adjacent separating containing fibrous layers 2, 4 and 6 are bonded together, i.e., fibrous layer 2 is bonded to fibrous layer 4, which in turn is bonded to fibrous layer 6. The bonding of each pair of adjacent fibrous layers is achieved in the region in which the respective intermediate layer is present by the application of heat and moderate pressure to melt the particles 12 of thermoplastic, polymeric, organic material that are respectively mixed with the particles of the absorbent gelling material 26 in the intermediate layer between the adjacent containing fibrous layers 2 and 4, and with the particles of the first odour control means 24 in the intermediate layer between the adjacent containing fibrous layer 4 and 6.

The bond between adjacent, separating, containing fibrous layers is generated by the melting of the individual particles 12 of thermoplastic, polymeric organic material; as it melts, the polymeric material forms "bridges", optionally comprising particles of absorbent gelling material 26 or of the first odour control means 24, which bridges connect the adjacent fibrous layers.

The overall surface area of the bond points represents a small fraction of the surface area of the fibrous layers 2, 4 and 6 and of the particles of the absorbent gelling material and of the odour control means, the characteristics of which thus remain almost unchanged.

Two continuous lines 18 of adhesive are also applied to the two sides of the intermediate layers on the longitudinal edge regions 16 of each pair of adjacent fibrous layers 2, 4 and 6 so as to prevent particles of absorbent gelling material 26 and of the first odour control means 24 from escaping from the longitudinal edges of the laminated structure 14, which correspond to the superposed edges of the containing, separating fibrous layers 2, 4 and 6, and also to reinforce the connection between the fibrous layers themselves.

Any other means for bonding the adjacent separating containing layers together, either in the region in which the respective intermediate layer is present, or along the respective longitudinal edges, can also be used anyway in alternate embodiments of the present invention, e.g. by means of sprayed adhesive or by fusion bonding, respectively.

The quantity of thermoplastic, polymeric, organic material in finely divided form that in a preferred embodiment can be distributed and mixed with the absorbent gelling material and with the odour control material is between 5 g/m2 and 180 g/m2.

The thermoplastic, polymeric, organic material can preferably be melted at a temperature such as not to interfere with the characteristics of the other components of the layered structure, i.e. the fibrous layers and the particulate material, namely the absorbent gelling material and the odour control means. Therefore, the thermoplastic material must have fluidity characteristics such as to enable the necessary bonds to be formed rapidly.

These preferred characteristics can be achieved by a thermoplastic, polymeric, organic material 7 having a melt flow index (M.F.I.), evaluated by the ASTM method D 1238-85 under conditions 190/2.16, of at least 25 g/10 min, preferably at least 40 g/10 min, and even more preferably at least 60 g/10 min.

If the fibrous layers 2, 4 and 6 are made of a dry-formed short cellulose fibre material, it is preferable to use a thermoplastic, polymeric, organic material composed of particles of high-density polyethylene with maximum dimensions of about 400 microns, characterized by a melt flow index of about 50 g/10 min, of which the quantity distributed is between 12 g/m2 and 90 g/m2.

The continuous lines 18 of adhesive disposed between the adjacent fibrous layers on the respective longitudinal edge portions prevent the particulate material forming the intermediate layers from escaping from the longitudinal edges of the structure. The laminated structure therefore can be produced separately and stored, for example, as a continuous strip wound in a roll which can subsequently be fed to the production line for disposable absorbent articles, for example sanitary napkins, where laminated absorbent structures 14 are manufactured from the continuous, laminated absorbent structure in order to be incorporated as absorbent elements in the absorbent articles.

Preferably the first odour control means 24 comprises the odour control agents whose activity is enhanced by reducing exposure of the agents to body fluids, i.e., which are more active when substantially not wetted by absorbed body fluids. Typically the odour control agents that are more sensitive to wetting are those, usually in particulate form, which are active towards gaseous odorous compounds by means of an adsorption mechanism, such as for example zeolites and activated carbon.

The laminated absorbent structure 14 can be incorporated in a disposable absorbent article, e.g. a sanitary napkin, as the absorbent element, being comprised between a fluid pervious topsheet and a fluid impervious backsheet.

In use, the laminated absorbent structure 14 incorporated as an absorbent element in a sanitary napkin is reached by body fluids on the first surface 20; the fluid is received by the first fibrous layer 2 and subsequently most of it is absorbed by the layer of absorbent gelling material 26 contained between the two adjacent containing fibrous layers 2 and 4. The first odour control means 24 contained between the two containing fibrous layers 4 and 6 can therefore act more effectively against gaseous odorous substances as the influence of wetness on the odour control agents that form the first odour control means is greatly reduced.

The absorbent gelling material 26 contained between the pair of separating containing fibrous layers 2 and 4 is capable of absorbing the body fluids, and at the same time has itself an odour control capability related to its pH-buffering and ion exchange properties: absorbent gelling materials are usually capable of keeping the pH of the fluid near neutrality at only slightly alkaline conditions, therefore controlling the formation of alkaline odorous compounds like ammonia and amines which are responsible of some unpleasant odours related to the use of absorbent articles.

Therefore a layer of absorbent gelling material contained between separating containing layers and combined with a first odour control means according to the present invention as above described not only increases the effectiveness of the odour control means substantially avoiding that such first odour control means is wetted by absorbed body fluids, but also keeping the pH of the absorbed fluid stable at nearly neutral values and performing a true odour control action against some alkaline odorous compounds.

A further advantage can be achieved in case a residual small amount of liquid should reach the first odour control means: not only in fact this amount is very small in any case, so that its possible influence on the activity of the first odour control means is low, but the pH value of the fluid that is kept near to neutrality further reduces this influence towards the first odour control means.

A synergic effect is therefore unexpectedly achieved by the combination of an absorbent gelling material and a first odour control means in a laminate absorbent structure according to the present invention.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used, as well as absorbent gelling material other than in a particulate form, e.g. in fibrous form.

The size of the absorbent gelling material particles may vary over a wide range. For reason of industrial hygiene, average particle sizes smaller than about 30 microns are less desirable. Particles having a smallest dimension larger than about 2 mm may also cause a feeling of grittyness in the absorbent article, which is undesirable from a consumer aesthetics standpoint. Furthermore, rate of fluid absorption can be affected by particle size. Larger particles have very much reduced rates of absorption. Preferred for use herein are absorbent gelling material s particles substantially all of which have a particle size of from about 30 microns to about 2 mm. "Particle size" as used herein means the weighted average of the smallest dimension of the individual particles.

The amount of absorbent gelling material particles used in the present invention will typically range from 20 g/m$^2$ to 150 g/m$^2$, preferably from 40 g/m$^2$ to 110 g/m$^2$, more preferably from 55 g/m$^2$ to 85 g/m$^2$.

The first odour control means 24 can comprise a single odour control agent, e.g. a zeolite, or, alternatively, a combination of different known odour control agents, preferably of the same type characterized by a better effectiveness in dry conditions. A mixture of zeolite and silica gel, both in particulate form, is particularly preferred, since the silica gel can perform both an odour control activity and an absorption action towards the residue moisture not completely absorbed by the absorbent gelling material, which should reach the first odour control means 24.

Zeolites may be naturally derived or synthetically manufactured. The synthetic zeolites being preferred for use herein and include zeolite A, zeolite P, zeolite Y, zeolite X, zeolite DAY, zeolite ZSM-5, and mixtures thereof. Most preferred are zeolite A and zeolite Y and mixtures thereof.

According to the present invention the zeolite is preferably hydrophobic. This is typically achieved by increasing the molar ratio of the $SiO_2$ to $AlO_2$ content such that the ratio of x to y is at least 1, preferably from 1 to 500, most preferably from 1 to 6.

The laminated absorbent structure preferably comprises from 40 g/m$^2$ to 90 g/m$^2$, more preferably from 55 g/m$^2$ to 85 g/m$^2$, most preferably from 60 g/m$^2$ to 65 g/m$^2$ of said zeolite.

The laminated absorbent structure preferably also comprises from 40 g/m² to 100 g/m², more preferably from 60 g/m² to 90 g/m², most preferably from 60 g/m² to 65 g/m² of silica, preferably silica gel, based on 100% purity.

The ratio of absorbent gelling material to silica to zeolite is preferably in the range of from 1:5:1 to 1:1:5, preferably from 1:3:1 to 1:1:3, most preferably from 1:1:1 to 1:1.5:1.5.

According to the present invention the weight of the first odour control means which may be used in the laminated absorbent structure can be readily determined by the skilled person bearing in mind the absorbent article dimensions. For example, when utilized in a sanitary napkin or panty liner, the laminated absorbent structure may comprise from 0.5 g to 5 g, preferably from 1 g to 3 g, most preferably from 1.5 g to 2.5 g of said odour control system.

According to the present invention the laminated absorbent structure 14 can comprise a second odour control means provided in at least a further layer interposed between the first surface 20 of the laminated absorbent structure 14 and the absorbent gelling material 26. Said second odour control means may comprise one or more optional components such as antimicrobial agents, perfuming ingredients, masking agents, pH-buffering systems, and chelants, all of which are known to the those skilled in the art. These optional odour control agents that constitute the second odour control means are preferably active in solution, i.e. when wetted by body fluids. They are therefore intended to be reached by the fluid first.

Odour control agents that constitute the second odour control means can be available in different forms, e.g. in powder form, or as an aqueous solution. Depending to their preferred form they can be comprised in the laminated absorbent structure 14 of the present invention in different arrangements. A second odour control means in solid form, e.g. in powder form, can be contained between a further containing fibrous layer, not illustrated in FIG. 1, and the first containing layer 2, or, alternatively, can be mixed with the absorbent gelling material 26. If the second odour control means is in form of an aqueous solution, it can be comprised within the containing layer which is nearer to the first surface 20, e.g. sprayed on the fibrous layer 2 of FIG. 1.

Suitable odour control agents to be used as second odour control means are those agents that at least reduce the enzymatic and/or bacterial activity within the absorbed fluid. Chelating agents as those described in European Applications EP 96109178.2 and EP 96109179.0, both applications filed on Jun. 7, 1996, are particularly preferred.

In an alternative preferred embodiment of the present invention, each single odour control agent that constitutes the first odour control means is contained between separating containing layers.

Figure 2:
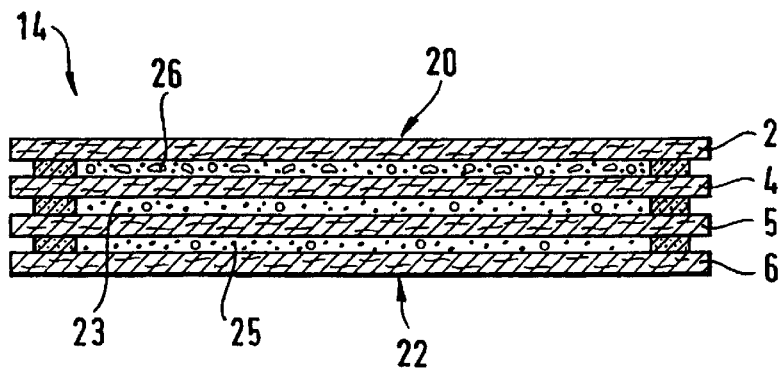
FIG. 2 is a sectional view of a laminated structure according to the present invention, similar to that illustrated in FIG. 1, but with four containing layers instead of three.

A preferred embodiment is illustrated in FIG. 2, in which a section of a laminated absorbent structure similar to that illustrated in FIG. 1 is shown. The first odour control means comprises the same preferred odour control agents already described, i.e. zeolite and silica gel in particle form, but each odour control agent is this time contained between separating containing layers, preferably fibrous layers of the same type described above. With respect to the embodiment of FIG. 1 there is one further separating containing fibrous layer 5 which separates the particles of silica gel 23 and of zeolite 25 that constitute the first odour control means 26. The zeolite 25 is disposed nearer to the second surface 22 of the laminated absorbent structure 14. The arrangement of each different odour control agent of the first odour control means 26 between separating containing layers can ensure an even better odour control action of the first odour control means, since possible interferences between different odour control agents are avoided. Moreover, the body fluid and moisture absorbing action of the absorbent gelling material 26 and of the silica gel 25, respectively, combined with their intrinsic odour control capability, increase to a higher extent the effectiveness of the zeolite 25 that can therefore act in a substantially anhydrous environment. In the preferred embodiment of FIG. 2 silica gel 25 can in fact act as an odour control agent, and at the same time is capable of absorbing the residue liquid or moisture that may reach it from the absorbent gelling material 26 and through the second containing layer 4. A second odour control means can be preferably incorporated in the laminated absorbent structure of FIG. 2, e.g. as an aqueous solution sprayed onto the first separating fibrous layer 2. Different odour control agents can therefore perform their action in the best conditions against different classes of odorous substances.

The containing layers comprised in the embodiments of the present invention described so far are preferably fibrous layers made of hydrophilic fibres, but they can also comprise non-fibrous layers, provided that they are fluid or at least gas permeable, e.g. layers constituted by one of the apertured polymeric films well known in the art.

Although the separating containing layers of the laminated absorbent structures described so far all have the same width which is constant along the length of the structure, further embodiments are also possible in which the separating containing layers have different widths, or, also, in which the width of the laminated absorbent structure can vary along the length of the structure itself, in order to provide, for example, a shaped absorbent element for a disposable absorbent article, e.g. an hourglass shaped one.

Alternatively, one or more of the hydrophilic separating containing fibrous layers of the laminated absorbent structures illustrated in FIGS. 1 and 2, preferably one or more of the intermediate containing layers, can be substituted by containing layers made of hydrophobic fibres, e.g. synthetic fibres.

In an alternate preferred embodiment the hydrophilic containing layer 5 of the embodiment illustrated in FIG. 2, and optionally the hydrophilic containing layer 4, can be replaced by layer(s) entirely made of hydrophobic synthetic fibres, e.g bicomponent fibres. Hydrophobic fibrous layers help to prevent residue fluid from reaching the zeolite particles 25, and the silica particles 23 as well if they constitute the containing layer 4 too, while at the same time, provide for the transmission of gaseous substances, e.g. malodorous compounds that can therefore reach the odour control agents of the first odour control means.

An intermediate containing layer made of synthetic fibres can have a further advantage if comprised in a laminated structure of the types described so far. An intermediate containing layer made of synthetic fibres can be used to bond the two adjacent containing layers together along the longitudinal edges 16 of the laminated structure 14 by simple application of heat and pressure, therefore avoiding the use of the continuous lines 18 of adhesive.

What is claimed is:

1. A laminated absorbent structure for absorbing aqueous body fluids and for providing odour control, said structure having a first surface intended to receive said fluids and a second surface aligned approximately opposite to said first surface, said laminated absorbent structure comprising first odour control means for absorbing malodours and further comprising an absorbent gelling material, said laminated absorbent structure being wherein said first odour control means and said absorbent gelling material are each contained between separating containing layers, said first odour control means being separated from said first surface by said absorbent gelling material.

2. A laminated absorbent structure according to claim 1, wherein it comprises a second odour control means provided in at least one further layer, said further layer being interposed between said first surface and said absorbent gelling material.

3. A laminated absorbent structure according to claim 2, wherein said first odour control means comprises one or more odour control agents that are active when substantially not wetted by said body fluids, and said second odour control means comprises one or more agents that are active when wetted by said body fluids.

4. A laminated absorbent structure according to claim 1, wherein each of said odour control agents of said first odour control means is contained between separating containing layers.

5. A laminated absorbent structure according to claim 2, wherein each of said odour control agents of said second odour control means is contained between separating containing layers.

6. A laminated absorbent structure according to claim 1, wherein said absorbent gelling material and said odour control agents are in particle or powder form.

7. A laminated absorbent structure according to claim 1, wherein said containing layers are fibrous layers.

8. A laminated absorbent structure according to claim 1, wherein each said absorbent gelling material and odour control agent constitute an intermediate layer between a respective pair of containing layers, each said intermediate layer also comprising a thermoplastic material, each said intermediate layer bonding the respective pair of containing layers together.

9. A laminated absorbent structure according to claim 8, wherein each said respective pair of containing layers extends beyond the intermediate layer contained therebetween, laterally forming longitudinal edge portions, each said respective pair of containing layers being bonded together along each of said edge portions by means of a continuous line of adhesive.

* * * * *